United States Patent [19]

Pöpel et al.

[11] Patent Number: 5,895,829
[45] Date of Patent: Apr. 20, 1999

[54] PREPARATION OF OLEFINICALLY UNSATURATED COMPOUNDS, IN PARTICULAR SYTRENE, BY CATALYTIC OXIDATION

[75] Inventors: Wolfgang Jürgen Pöpel, Darmstadt; Alfred Hagemeyer; Wolfgang Büchele, both of Ludwigshafen; Axel Deimling, Neustadt; Wolfgang Hoffmann, Frankenthal, all of Germany

[73] Assignee: BASF Aktiengesellschaft, Ludwigshafen, Germany

[21] Appl. No.: 08/849,712

[22] PCT Filed: Dec. 12, 1995

[86] PCT No.: PCT/EP95/04895

§ 371 Date: Jun. 18, 1997

§ 102(e) Date: Jun. 18, 1997

[87] PCT Pub. No.: WO96/20149

PCT Pub. Date: Jul. 4, 1996

[30] Foreign Application Priority Data

Dec. 23, 1994 [DE] Germany ............... 44 46 384

[51] Int. Cl.⁶ .................................................. C07C 5/42
[52] U.S. Cl. ............... 585/444; 585/445; 585/654; 585/658; 585/662; 585/663; 208/134; 208/136; 208/141
[58] Field of Search ............... 585/444, 445, 585/654, 658, 662, 617, 627, 630, 631; 208/134, 136, 141

[56] References Cited

U.S. PATENT DOCUMENTS

| | | | |
|---|---|---|---|
| 3,440,299 | 4/1969 | Woskow et al. | 260/680 |
| 3,488,402 | 1/1970 | Michaels et al. | 260/680 |
| 3,567,793 | 3/1971 | Colling et al. | 260/680 |
| 3,686,347 | 8/1972 | Dean et al. | 260/680 E |
| 4,568,789 | 2/1986 | Withers, Jr. | 585/654 |
| 4,581,339 | 4/1986 | Bhatt et al. | 502/38 |
| 4,704,497 | 11/1987 | Gottlieb et al. | 585/654 |
| 4,795,849 | 1/1989 | Gaffney et al. | 585/500 |

FOREIGN PATENT DOCUMENTS

| | | |
|---|---|---|
| 179 869 | 5/1986 | European Pat. Off. |
| 254 423 | 1/1988 | European Pat. Off. |
| 403 462 | 12/1990 | European Pat. Off. |
| 543 535 | 5/1993 | European Pat. Off. |
| 556 489 | 8/1993 | European Pat. Off. |
| 558 148 | 9/1993 | European Pat. Off. |
| 999 629 | 7/1965 | United Kingdom. |
| 2 156 842 | 10/1985 | United Kingdom. |

OTHER PUBLICATIONS

Jr. of Catalysis 12, 281–290 (1968) Reduction of $Bi_2O_3$–$MoO_3$ Catalyst during the Ammoxidation . . . Aykan.

*Primary Examiner*—Bekir L. Yildirim
*Attorney, Agent, or Firm*—Keil & Weinkauf

[57] ABSTRACT

In a process for preparing olefinically unsaturated compounds such as styrene by oxidative dehydrogenation of corresponding hydrocarbons using a previously oxidized oxygen transferer acting as catalyst in the absence of molecular oxygen and reoxidation of the oxygen transferer in at least two reactors, the dehydrogenation and regeneration takes place alternately in time in the two reactors and the reactors are connected to one another in terms of heat via heat exchangers and a common circuit for heat transfer medium.

14 Claims, No Drawings

PREPARATION OF OLEFINICALLY UNSATURATED COMPOUNDS, IN PARTICULAR SYTRENE, BY CATALYTIC OXIDATION

The invention relates to a process for preparing olefinically unsaturated compounds by catalytic oxygen transfer from a previously oxidized oxygen transferer acting as catalyst to corresponding hydrocarbons (dehydrogenation) in the absence of molecular oxygen. The invention preferably relates to the catalytic oxidative dehydrogenation of alkylaromatics and paraffins to give the corresponding alkenylaromatics and olefins, in particular the dehydrogenation of ethylbenzene to give styrene, with water being formed.

styrene and divinylbenzene are important monomers for industrial plastics and are used in large quantities.

Styrene is prepared predominantly by non-oxidative dehydrogenation of ethylbenzene over modified iron oxide catalysts, with one mole of hydrogen being formed per mole of styrene. A disadvantage of this reaction is that it is an equilibrium reaction which typically proceeds at from 600 to 700° C. and gives a conversion of about 60% at a styrene selectivity of about 90%. As the conversion and concentration of the target product rise, the reverse reaction occurs and limits the conversion.

Oxidative dehydrogenation, in which the hydrocarbon is reacted with molecular oxygen, enables, in contrast, a virtually quantitative conversion to be achieved, since water is formed in this reaction. In addition, this reaction proceeds at a lower temperature than the non-oxidative dehydrogenation. A disadvantage of this procedure is that carbon monoxide and dioxide are formed in a secondary reaction (total oxidation).

It has therefore been proposed that, instead of using molecular oxygen, use be made of an oxygen transferer comprising a reducible metal oxide which acts as catalyst, ie. steers the reaction. In the process the oxygen transferer gradually becomes exhausted and is regenerated in a second step. This principle, which is frequently used in classical process engineering, is called the regenerative principle or non-steady-state method. In the case of the oxidative dehydrogenation, the enthalpy balance of the overall reaction, ie. the sum of the two sub-steps, is negative. By decoupling the reduction and oxidation steps, the selectivity can be significantly increased.

The regenerative principle using a reducible and regenerable catalyst was first described for the oxidation or ammonoxidation of propene to give acrolein and acrylic acid or acrylonitrile (GB 885 422; GB 999 629; K. Aykan, J. Catal. 12 (1968) 281–190), with arsenate and molybdate catalysts being used. The use of the regenerative process in the oxidative dehydrogenation of aliphatic alkanes to give monoolefins and diolefins using ferrite catalysts (eg. U.S. Pat. No. 3,440,299, DE 21 18 344, DE 17 93 499) is likewise known, as is its use for the oxidative coupling of methane to give higher hydrocarbons; catalysts having various structures are used here (Mn/Mg/Si oxides in U.S. Pat. No. 4,795,849, DE 35 86 769; ruthenium oxide in U.S. Pat. No. 4,568,789; Mn/B oxides on MgO in EP 254 423; $Mn_3O_4$ spinels in GB 2 156 842). Also known is the dehydrodimerization of toluene to give stilbene in the absence of free oxygen by means of reducible catalysts such as Bi/In/Ag oxides (EP 30 837). Finally, the principle has also been used in the dehydrogenation, dehydrocyclization and dehydroaromatization of paraffin hydrocarbons for upgrading gasoline (U.S. Pat. No. 4,396,537, using Co/P oxide catalysts).

EP 397 37 and 403 462 disclose the use of the process principle for the oxidative dehydrogenation of paraffinic hydrocarbons and alkylaromatics. According to these disclosures, use is made of reducible oxides of metals selected from the group V, Cr, Mn, Fe, Co, Pb, Bi, Mo, U and Sn applied to supports of clays, zeolites and oxides of Ti, Zr, Zn, Th, Mg, Ca, Ba, Si, Al.

The listing above is only an extract from the extensive literature and relates only to processes which are relatively similar chemically. Without going into more detail, further information is to be found in the following publications: EP 558 148; EP 556489; EP 543535; U.S. Pat. No. 3,488,402.

Industrially, there are two versions of the decoupling, namely the separation of the two sub-steps in space or in time.

In the separation in space of the two sub-steps, a moving bed or a circulating fluidized bed is used, with the catalyst particles being conveyed from the dehydrogenation zone, after separating off the reaction products, to a separate regeneration reactor in which the reoxidation proceeds. The regenerated catalyst is returned to the dehydrogenation zone. Such a process can be carried out continuously, ie. cyclically. The catalyst is subjected to high mechanical stresses and must therefore have sufficient hardness.

Separation in time can be achieved using a fixed-bed oxygen transferer/catalyst, with periodic switching between hydrocarbon feed, ie. the productive reaction, and regeneration.

The cited documents describe processes for carrying out non-steady-state oxidations. The recovery of the heat liberated and the coupling of a plurality of alternately operated reactors to give an integrated heat system has hitherto not been described.

The establishment of integrated heat systems, ie. the coupling in terms of heat of two different reactions of which one is exothermic and the other is endothermic and both are operated in a steady-state manner, ie. without switching, is known per se.

Thus, NE-A-93 00 168 describes the combination of an exothermic oxidative reaction of methane with an endothermic reaction not specified in more detail, with heat exchange always taking place in the same direction from the first to the second reaction.

It is an object of the present invention to provide, for a process of the type mentioned in the introduction, a method of operation and apparatus enabling the reliable recovery of the net enthalpy of this process, as economically as possible and with little outlay in terms of apparatus.

A very high space-time yield of the productive reaction and, by means of improved heat management in the dehydrogenation, reduction of the amount of byproduct and thus an efficient usage of raw material are also to be achieved.

We have found that this object is achieved by a process of the type mentioned in the introduction in which at least two reactors containing a catalyst for the oxidative dehydrogenation and each having at least one heat exchanger, in which reactors the dehydrogenation and regeneration takes place alternately in time, are coupled to form an integrated heat system by the heat exchangers being connected to one another in terms of heat by means of a common circuit for heat transfer medium.

The net enthalpy obtained is advantageously drawn from the heat transfer circuit at a suitable point in a manner known per se in such a way that it can be usefully utilized at another point.

The heat transfer medium can be a heat transfer gas or, for example, a salt melt. Organic heat transfer media are less suitable because of the high temperature level; a particularly advantageous heat transfer gas is hot steam which, for example by injection of water, can easily be maintained at the most suitable temperature in each case, for which purpose extensive technology is available.

The amounts of heat liberated in the regeneration or taken up in the productive reaction can be calculated from the respective reaction enthalpies which can in turn be obtained from the standard enthalpies of formation.

The sub-steps in a non-steady-state procedure using an oxygen-transferring redox catalyst comprise dehydrogenation (about 90% styrene yield) and regeneration of the catalyst, where (for the example of the system $V_2O_5/V_2O_3$) the dehydrogenation proceeds endothermically with an enthalpy of formation of +42.1 kJ/mol at 500° C. while the regeneration is exothermic at −164.2 kJ/mol.

It can be seen from this that the net enthalpy of the oxidative dehydrogenation represents a considerable amount of heat which is additionally made available at a thermodynamically desirable high level, so that after the process of the invention the heat liberated can be utilized directly, ie. without, for instance, using heat pumps or the like, for generating, for example, useful hot steam and to drive modern power generation equipment.

It is also advantageous that the endothermic productive reaction, namely the dehydrogenation of, for example, ethylbenzene, proceeds at a temperature which is about 100° lower than that of the exothermic regeneration, so that it can easily be arranged for the residual heat remaining after drawing off the net enthalpy to be made available at exactly the temperature level required for operating the endothermic productive reaction.

In a suitable arrangement, a plurality of reactors (their total number being n) are connected to form an integrated system in such a way that in mutual alternate operation a certain number of reactors (m reactors, where m<n) are in the dehydrogenation phase while at the same time the remaining n-m reactors are in the regeneration phase. In the switching over procedure, the required number of reactors are then switched from dehydrogenation to regeneration and the same number of reactors are switched from regeneration to dehydrogenation.

In the simplest case, two alternately operated fixed-bed reactors, are used. In the circulated gas or salt melt circuit which supplies heat to the reactor which is at the time in the dehydrogenation phase and removes heat from the reactor which is at the time in the regeneration phase, there is provided a heat exchanger by means of which steam can be generated and fed into the network of a larger integrated steam system. In the phase change, the reactor which has served for dehydrogenation is regenerated and the other reactor is used for the productive reaction. A prerequisite here is that the required dehydrogenation and regeneration times are approximately equal.

Naturally, more than 2 reactors can also be connected to form an integrated system. If, for instance, the regeneration is slower than the dehydrogenation, 3 reactors, for example, can be coupled in alternate operation in such a way that dehydrogenation is carried out in one reactor while regeneration is carried out in the other 2 reactors and at the next phase change the chain is then moved on by one reactor in each case. If on the contrary the regeneration is faster than the dehydrogenation, one reactor will be operated in the regeneration phase and the other two in the dehydrogenation phase. The relative rates of dehydrogenation and regeneration depend on the chemical nature of the raw material in each case and on the reaction temperature selected. Fundamentally, the greater the number of reactors available, the better the required dehydrogenation and regeneration periods can be matched to one another and thus the space-time yield can be optimized.

Oxidation/dehydrogenation processes used in industry are carried out at from 100 to 900° C., preferably from 250 to 750° C., and at pressures of from 100 mbar to 10 bar, preferably from 500 mbar to 2 bar, at an LHSV (liquid hourly space velocity) of from 0.01 to 20 $h^{-1}$, preferably from 0.1 to 5 $h^{-1}$. In addition to the hydrocarbon to be oxidized/dehydrogenated, diluents such as $CO_2$, $N_2$, noble gases or steam can be present.

Specifically for the oxidative dehydrogenation to give compounds of the styrene type, a suitable catalyst advantageously comprises at least one reducible metal oxide selected from the group of the oxides of Ce, Cr, V, Mn, Fe, Co, Nb, Mo, Wo, In, Cu, Ag, Sn, Pb, Sb or Bi, which can be either unsupported or applied to a support which can be selected from the group of clays, pillared clays (PILC), zeolites, aluminum phosphates, SiC, $Si_3N_4$, BN, C (graphite) and/or the metal oxides selected from the group of the oxides of Ti, Zr, Zn, Th, Mg, Ca, Ba, Si, Al, and can additionally comprise promoters, in particular alkali metals, alkaline earth metals and/or rare earths.

The regeneration of the exhausted catalyst is carried out in the range from 100 to 800° C., preferably from 250 to 600° C., using a free oxidant, preferably using $N_2O$ or an oxygen-containing gas including pure oxygen. Here too, diluents can be present in the regeneration stream. Suitable regeneration gases are, for example, air, lean air, oxygen or $N_2O$. The regeneration can be carried out at subatmospheric, atmospheric or superatmospheric pressure. Preference is given to pressures in the range from 500 mbar to 10 bar.

The residence time in the dehydrogenation can be, for example, in the range from 0.01 to 20 seconds, preferably from 0.05 to 5 and particularly preferably in the range from 0.1 to 3 seconds.

The residence time in the regeneration can be, for example, in the range from 0.01 to 100 seconds, preferably from 0.05 to 50 and particularly preferably in the range from 0.1 to 30 seconds.

All conventional catalysts which have been prepared by any desired methods and are suitable for use in a fixed bed or even for use in a fluidized bed can be used for the process of the invention. Preferred catalysts comprise at least one reducible bismuth and/or cerium and/or vanadium catalyst which may be applied to a support, for example on the basis of titanium and/or chromium oxide, and may be further promoted using an alkali metal, alkaline earth metal and/or rare earth metal.

EXAMPLE 1

For the preparation of a catalyst comprising vanadium on a magnesium oxide support, 336.3 g of ammonium metavanadate and 900 g of magnesium oxide are stirred into 8 l of water and the stirring is continued for one hour. The powder obtained in a spray dryer is made up to a paste with a little water and an extrusion aid, processed for 2 hours in a laboratory compounder and then shaped into 3 mm extrudates which were dried for 16 hours at 120° C., calcined at 600° C. and comminuted. This catalyst contains 22.5% of $V_2O_5$ and 77.5% of MgO. For the tests, a particle size fraction of from 0.5 to 0.7 mm was sieved out.

A helical laboratory reactor is charged with 9.3 g of the catalyst so that the catalyst volume in the reactor is 20 ml. The reactor is, for the purpose of heating, located in a salt melt maintained at 500° C. The gas stream leaving the reactor can be condensed, collected and analyzed by GC.

10 ml/h of ethylbenzene are taken from a reservoir by means of a pump and vaporized in a stream of nitrogen in such a way that the nitrogen flow (for setting the residence time) is from 8 to 28 standard l/h. The residence time thereby obtained is from 0.8 to 3 seconds. As can be easily calculated, the LHSV is $0.5\ h^{-1}$.

Dehydrogenation and regeneration phase each take 5 minutes, ie. a complete cycle takes 10 minutes.

When using only one reactor in the salt bath, 0.51 g of styrene are obtained per cycle, corresponding to a space-time yield (STY) of 0.33 kg of styrene per kg of catalyst and hour. When the experimental apparatus is appropriately doubled up and operated in the integrated system of the invention, an STY of 0.41 kg of styrene per kg of catalyst and hour is achieved.

EXAMPLE 2

In a laboratory apparatus, the isothermal oxidative dehydrogenation of ethylbenzene to give styrene is carried out at 500° C. and an LHSV of $0.5\ h^{-1}$. The catalyst described in Example 1 is here first reduced during the dehydrogenation and, after changing the feed stream to air, is reoxidized. The cycle time (reduction and oxidation step) is 10 minutes. A selectivity of 95% is achieved at a conversion of 95% of ethylbenzene.

In the laboratory apparatus, the excess amount of heat (corresponding to the amount of heat which can theoretically be transferred out) after subtracting the weakly endothermic oxidative dehydrogenation (including catalyst reduction) is 1.7 W.

Comparative experiment: In the non-oxidative dehydrogenation of ethylbenzene to give styrene, a selectivity of 94% is achieved at about 600° C. and an ethylbenzene conversion of 60%. The STY is about 0.2.

We claim:

1. A process for preparing olefinically unsaturated compounds by catalytic oxygen transfer from a previously oxidized oxygen transferer acting as catalyst to corresponding hydrocarbons (dehydrogenation) in the absence of molecular oxygen and regeneration (reoxidation) of the oxygen transferer, wherein at least two reactors each containing a catalyst for the oxidative dehydrogenation and each having at least one heat exchanger, in which reactors the dehydrogenation and regeneration takes place alternately in time, are coupled to form an integrated heat system by the heat exchangers being connected to one another in terms of heat by means of a common circuit for heat transfer medium.

2. A process as claimed in claim 1, wherein the heat transfer medium used is a circulating gas or a salt melt.

3. A process as claimed in claim 1, wherein a net amount of heat is drawn from the circuit for heat transfer medium and is used outside the process.

4. A process as claimed in claim 1, wherein the sub-steps dehydrogenation and reoxidation are decoupled in time in such a way that, using a fixed catalyst bed, the reactor inlet stream is periodically switched between the starting materials and the regeneration gas.

5. A process as claimed in claim 1, wherein between the dehydrogenation step and the regeneration step there is inserted a flushing phase in which a flushing gas flows through the fixed bed reactor.

6. A process as claimed in claim 1, wherein the hydrocarbons to be dehydrogenated are alkylaromatics which are dehydrogenated to give the corresponding alkenylaromatics.

7. A process as claimed in claim 6, wherein ethylbenzene is dehydrogenated by catalytic oxidative dehydrogenation using a redox catalyst to give styrene.

8. A process as claimed in claim 1, wherein the reduced catalyst is regenerated using an oxygen-containing gas or pure oxygen.

9. A process as claimed in claim 1, wherein the reduced catalyst is regenerated using $N_2O$ as oxidant.

10. A process as claimed in claim 1, wherein the catalyst used comprises at least one reducible metal oxide selected from the group of the oxides of Ce, Cr, V, Mn, Fe, Co, Nb, Mo, Wo, In, Cu, Ag, Sn, Pb, Sb or Bi, either unsupported or on a support.

11. A process as claimed in claim 10, wherein the catalyst is applied to a support selected from the group of clays, pillared clays (PILC), zeolites, aluminum phosphates, silicon nitride and carbide, boron nitride and carbide, graphite and/or the metal oxides selected from the group of the oxides of Ti, Zr, Zn, Th, Mg, Ca, Ba, Si, Al, and can additionally comprise promoters, in particular alkali metals, alkaline earth metals and/or rare earths.

12. A process as claimed in claim 11, wherein the catalyst comprises at least one reducible oxide of bismuth, vanadium or cerium on a titanium oxide or chromium oxide support.

13. A process as claimed in claim 10, wherein the catalyst comprises a promoter selected from the group of alkali, alkaline earth and/or rare earth metals.

14. A process as claimed in claim 10, whose dehydrogenating sub-step is carried out at from 200 to 800° C., at a pressure of from 100 mbar to 10 bar and at an LHSV of from 0.01 to 20 $h^{-1}$.

* * * * *